United States Patent [19]

Sih

[11] 4,220,758
[45] Sep. 2, 1980

[54] $C_{1-4}$ ALKANOYLPHENYL-ESTERS OF 5-HYDROXY-PGI$_1$, $\Delta^4$-PGI$_1$, AND 4-OXO-PGI$_1$ COMPOUNDS

[75] Inventor: John C. Sih, Kalamazoo, Mich.

[73] Assignee: The Upjohn Company, Kalamazoo, Mich.

[21] Appl. No.: 48,494

[22] Filed: Jun. 14, 1979

Related U.S. Application Data

[62] Division of Ser. No. 933,329, Aug. 14, 1978, Pat. No. 4,180,657.

[51] Int. Cl.$^2$ ................. C07D 307/93; C07D 311/94;

[52] U.S. Cl. .................................. 542/426; 542/429; 260/345.2; 260/346.22

[58] Field of Search .................... 260/346.22, 345.2 R; 542/426, 429

[56] References Cited

PUBLICATIONS

Johnson et al., Prostaglandins, May 1978, vol. 15, No. 5, pp. 737–750.

*Primary Examiner*—Henry R. Jiles
*Assistant Examiner*—Bernard Dentz
*Attorney, Agent, or Firm*—Robert A. Armitage

[57] ABSTRACT

Acyl-substituted phenyl esters of prostacyclin-type compounds, for example the 4-acetylphenyl ester of prostacyclin (PGI$_2$) illustrated by the formula

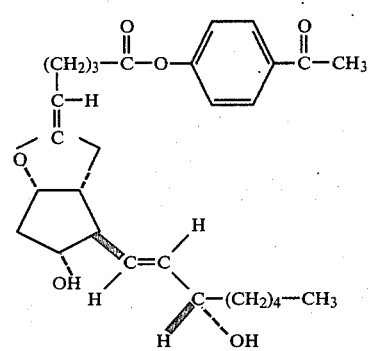

and including esters of the isomeric 6-hydroxy-PGI$_1$ and 6-keto-PGF$_{1\alpha}$ compounds, said esters having pharmacological activity. Processes for preparing them and the appropriate intermediates are disclosed.

25 Claims, No Drawings

//=====

$C_{1-4}$ ALKANOYLPHENYL-ESTERS OF 5-HYDROXY-PGI$_1$, $\Delta^4$-PGI$_1$, AND 4-OXO-PGI$_1$ COMPOUNDS The present application is a divisional application of Ser. No. 933,329, filed Aug. 14, 1978, now issued as U.S. Pat. No. 4,180,657, on Dec. 25, 1979.

The present invention relates to prostaglandin analogs for which the essential material constituting a disclosure therefor is incorporated by reference here from U.S. Pat. No. 4,180,657, issued Dec. 25, 1979.

I claim:

1. An acid ester of a prostacyclin analog of the formula

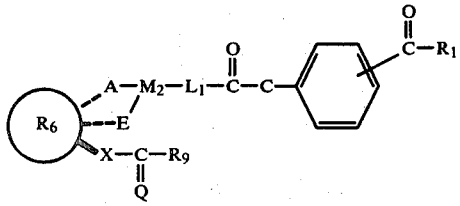

wherein A is (1) —O-(oxa) or, when E is —CH$_2$—, (2) —CH$_2$—O—, with —CH$_2$ bonded to R$_8$
wherein E is —CH$_2$— or —CH$_2$CH$_2$—,
wherein L$_1$ is
 (1) —(CH$_2$)$_n$— wherein n is one to 5, inclusive,
 (2) —(CH$_2$)$_p$—CF$_2$— wherein p is one 2, 3, or 4, or
 (3) —(CH$_2$)$_v$—CH=CH— wherein v is zero 1, 2, or 3,
when M$_2$ is

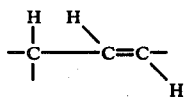

or L, is (1)—(CH$_2$)$_n$—wherein n is one to 5 inclusive,
 (2)—(CH$_2$)$_p$—CF$_2$—wherein p is 2, 3 or 4, or
 (3)—(CH$_2$)$_v$—CH=CH—wherein V is 1,2 or 3, and M$_2$ is

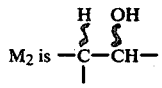

wherein ~ indicates attachment in cis or trans configuration
wherein Q is

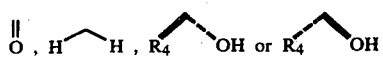

wherein R$_4$ is hydrogen or alkyl of one to 4 carbon atoms, inclusive,
wherein R$_1$ is alkyl of one to 4 carbon atoms, inclusive, with the proviso that when R$_1$ is tert-butyl the —C(O)—R$_1$ group is in the 4-position, wherein R$_8$ is

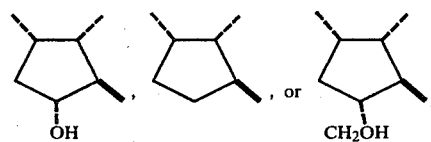

and wherein R$_9$ is

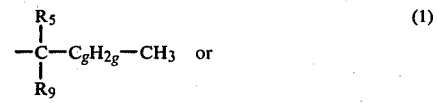

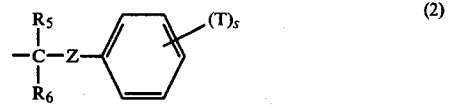

wherein C$_9$H$_{2]}$is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—);
wherein Z represents an oxa atom (—O—) or C$_j$H$_{zj}$ wherein C$_j$H$_{2j}$ is a valence bond or alkylene of one to 9 carbon atoms, inclusive, with one to 6 carbon atoms, inclusive between CR$_5$R$_6$— and the phenyl ring;
wherein T is alkyl of one to 4 carbon atoms, inclusive, fluoro, chloro, trifluoromethyl, or —OR$_7$— wherein R$_7$ is alkyl of one to 4 carbon atoms, inclusive, and s is zero, one, 2 or 3, with the proviso that not more than two T's are other than alkyl and when s is 2 or 3 the T's are either the same or different, and
wherein X is
 (1) trans-CH=CH—
 (2) cis-CH=CH—
 (3) —C≡C— or
 (4) —CH$_2$CH$_2$—.

2. (5S and 5R)-5-Hydroxy-(6S)-PGI$_1$, 4-acetylphenyl ester, compounds according to claim 1.

3. (5S and 5R)-5-Hydroxy-(6R)-PGI$_1$, 4-acetylphenyl ester, compounds according to claim 1.

4. (5S and 5R)-5-Hydroxy-(15S)-15-methyl-(6S)-PGI$_1$, 4-acetylphenyl ester, compounds according to claim 1.

5. (5S and 5R)-5-Hydroxy-16,16-dimethyl-(6S)-PGI$_1$, 4-acetylphenyl ester, compounds according to claim 1.

6. (5R)-5-Hydroxy-13,14-didehydro-(6S)-PGI$_1$, 4-acetylphenyl ester, a compound according to claim 1.

7. (5R)-5-Hydroxy-2,2-difluoro-(6S)-PGI$_1$, 4-acetylphenyl ester, a compound according to claim 1.

8. (5R)-5-Hydroxy-16-Phenoxy-17,18,19,20-tetranor-(6S)-PGI$_1$, 4-acetylphenyl ester, a compound according to claim 1.

9. Trans-$\Delta^4$-(6R)-PGI$_1$, 4-acetylphenyl ester, a compound according to claim 1.

10. Trans-$\Delta^4$-(6S)-PGI$_1$, 4-acetylphenyl ester, a compound according to claim 1.

11. Trans-$\Delta^4$-13,14-didehydro-(6R)-PGI$_1$, 4-acetylphenyl ester, a compound according to claim 1.

12. Trans-$\Delta^4$-13,14-didehydro-(6R,15R)-PGI$_1$, 4-acetylphenyl ester, a compound according to claim 1.

13. Trans-$\Delta^4$-2,2-difluoro-16,16-dimethyl-(6R)-PGI$_1$, 4-acetylphenyl ester, a compound according to claim 1.

14. Trans-$\Delta^4$-(15S)-15-methyl-(6R)-PGI$_1$, 4-acetylphenyl ester, a compound according to claim 1.

15. Trans-$\Delta^4$-16,16-dimethyl-(6R)-PGI$_1$, 4-acetylphenyl ester, a compound according to claim 1.

16. Trans-$\Delta^4$-16,16-difluoro-(6R)-PGI$_1$, 4-acetylphenyl ester, a compound according to claim 1.

17. Trans-$\Delta^4$-13,14-didehydro-(6S)-PGI$_1$, 4-acetylphenyl ester, a compound according to claim 1.

18. Trans, trans-$\Delta^2,\Delta^4$-(6S)-PGI$_1$, 4-acetylphenyl ester, a compound according to claim 1.

19. Trans, trans-$\Delta^2,\Delta^4$-16,16-dimethyl-(6S)-PGI$_1$, 4-acetylphenyl ester, a compound according to claim 1.

20. Trans, trans-$\Delta^2,\Delta^4$-13,14-didehydro-(6R)-PGI$_1$, 4-acetylphenyl ester, a compound according to claim 1.

21. Trans, trans-$\Delta^2,\Delta^4$-(6R)-PGI$_1$, 4-acetylphenyl ester, a compound according to claim 1.

22. Trans, trans-$\Delta^2,\Delta^4$-16,16-dimethyl-(6R)-PGI$_1$, 4-acetylphenyl ester, a compound according to claim 1.

23. Trans, trans-$\Delta^2,\Delta^4$-16,16-difluoro-(6R)-PGI$_1$, 4-acetylphenyl ester, a compound according to claim 1.

24. An acid ester of a prostacyclin analog of the formula

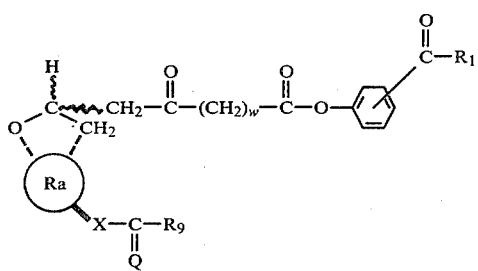

wherein Q is

wherein R$_4$ is hydrogen or alkyl of one to 4 carbon atoms, inclusive, wherein R$_1$ is alkyl of one to 4 carbon atoms, inclusive, with the proviso that when R$_1$ is tert-butyl the

group is in the 4-position,
wherein R$_8$ is

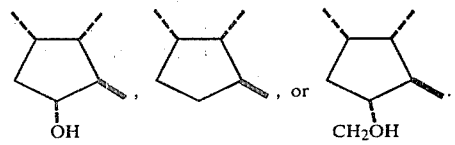

wherein R$_9$ is

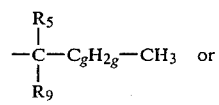

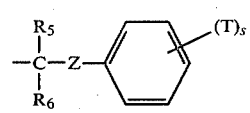

wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—);

wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR$_5$R$_6$— and the phenyl ring;

wherein T is alkyl of one to 4 carbon atoms; inclusive, fluoro, chloro, trifluoromethyl, or —OR$_7$— wherein R$_7$ is alkyl of one to 4 carbon atoms, inclusive, and s is zero, one, 2 or 3, with the proviso that not more than two T's are other than alkyl and when s is 2 or 3 the T's are either the same or different, wherein X is
(1) trans-CH=CH—
(2) cis-CH=CH—
(3) -C≡C— or
(4) —CH$_2$CH$_2$—,
wherein w is one, 2, or 3, and
wherein ~ indicates attachment in cis or trans configuration.

25. (6R and 6S)-4-Oxo-PGI$_1$, 4-acetylphenyl ester, compounds according to claim 24.

* * * * *

UNITED STATES PATENT OFFICE
CERTIFICATE OF CORRECTION

Patent No. 4,220,758   Dated 2 September 1980

Inventor(s) John C. Sih

It is certified that error appears in the above-identified patent and that said Letters Patent are hereby corrected as shown below:

Column 1, lines 17-25, that portion of the formula reading

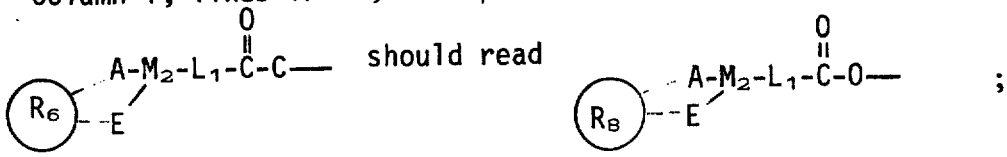

line 35, "when $M_2$ is" should read -- and $M_2$ is --
line 45, "or L is" should read -- or $L_1$ is --; line 48 and 52, "$M_2$ is $M_2$ is" should read -- $M_2$ is --;

Column 2, lines 13-15 and Column 4, lines 18-21,

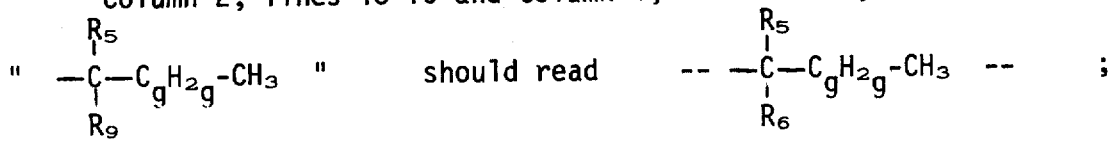

Column 2, line 22, "$C_9H_{21}$ is" should read -- $C_gH_{2g}$ is --;
line 31, "$C_jH_{zj}$" should read -- $C_jH_{2j}$ --;

Column 3, lines 37-46, that portion of the formula reading

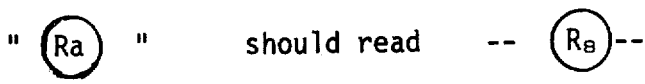

Signed and Sealed this

Sixteenth Day of June 1981

[SEAL]

Attest:

RENE D. TEGTMEYER

Attesting Officer   Acting Commissioner of Patents and Trademarks